United States Patent [19]

Suzuki

[11] 4,057,577
[45] Nov. 8, 1977

[54] PROCESS FOR PREPARING DI(ALKOXY-CARBOXY) HYDROCARBYLENES

[75] Inventor: Shigeto Suzuki, San Francisco, Calif.

[73] Assignee: Chevron Research Company, San Francisco, Calif.

[21] Appl. No.: 711,934

[22] Filed: Aug. 5, 1976

[51] Int. Cl.$^2$ .............................................. C07C 59/22
[52] U.S. Cl. ........................... 260/535 P; 260/514 K; 260/520 B; 260/521 P; 260/535 R
[58] Field of Search ........... 260/535 R, 535 P, 514 K, 260/521 P, 520 B

[56] References Cited

U.S. PATENT DOCUMENTS

| 3,948,977 | 4/1976 | Suzuki | 260/535 R |
| 3,948,986 | 4/1976 | Suzuki | 260/535 R |

*Primary Examiner*—Paul J. Killos
*Attorney, Agent, or Firm*—D. A. Newell; John Stoner, Jr.; W. Keith Turner

[57] ABSTRACT

A process for preparing di(alkoxycarboxy) hydrocarbylenes which comprises contacting carbon monoxide with a saturated aldehyde and a non-adjacent dihydric alcohol in the presence of a catalytic amount of hydrogen fluoride.

11 Claims, No Drawings

PROCESS FOR PREPARING DI(ALKOXY-CARBOXY) HYDROCARBYLENES

BACKGROUND OF THE INVENTION

The process of this invention relates to the reaction of carbon monoxide with a saturated aldehyde and a non-adjacent dihydric alcohol to obtain a di(alkoxycarboxy) hydrocarbylene of the formula

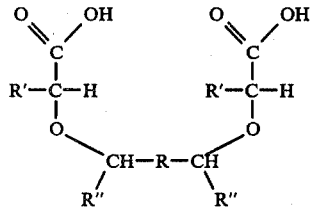

wherein R is straight or branched chain alkylene, oxaalkylene or cycloalkylene; each R' is hydrogen or straight or branched chain alkyl; and each R'' is hydrogen, straight or branched alkyl, arylalkyl, haloalkyl or oxaalkyl. In particular, the process concerns the use of hydrogen fluoride to catalyze the reaction which leads to the formation of the di(alkoxycarboxy) hydrocarbylenes.

Di(alkoxycarboxy)-substituted compounds, such as those prepared by this process, are useful in the production of polymyers. For instance, they react with polyols to form liquid or rigid polyesters which are useful for uses such as vinyl plasticizers, unsaturated polyesters and molding resins.

U.S. Pat. No. 3,948,986, granted Apr. 6, 1976, describes a process for preparing alpha-hydroxy carboxylic acids by contacting carbon monoxide with a saturated $C_2$–$C_{16}$ aldehyde and water in the presence of a hydrogen fluoride catalyst. Similarly, U.S. Pat. No. 3,948,977, granted Apr. 6, 1976, describes a process for preparing alkoxyacetic acid by contacting carbon monoxide with formaldehyde and a mono-hydric alcohol in the presence of hydrogen fluoride.

SUMMARY OF THE INVENTION

This invention provides a process for preparing di(alkoxycarboxy) hydrocarbylenes which comprises contacting carbon monoxide with a saturated aldehyde and a non-adjacent dihydric alcohol in the presence of a catalytic amount of hydrogen fluoride at a temperature of from about 0° to about 100° C and a carbon monoxide partial pressure of from about 10 psia to about 4000 psia.

DETAILED DESCRIPTION OF THE INVENTION

The process of this invention is based upon the discovery that hydrogen fluoride will catalyze the reaction of carbon monoxide with a saturated aldehyde and a non-adjacent dihydric alcohol to produce a di(alkoxycarboxy) hydrocarbylene or a di(alkoxycarboxy)oxahydrocarbylene. The reaction is carried out under moderate reaction conditions.

The saturated aldehydes used in the process are preferably $C_1$ to $C_{20}$ saturated aldehydes, more preferably $C_1$ to $C_6$ saturated aldehydes. The term "saturated aldehyde" as used herein, includes aldehydes wherein the aldehyde functional group is attached to a saturated group — that is, an alkyl group. Representative aldehydes which may be used in this process include, formaldehyde, acetaldehyde, propionaldehyde, butyraldehyde, caprylaldehyde, and the like.

The non-adjacent dihydric alcohols used in the process are preferably $C_3$ to $C_{20}$ $\alpha$, $\omega$-alkanediols, more preferably $C_3$ to $C_{10}$ alkanediols. The term "non-adjacent dihydric alcohol" as used herein, includes alcohols having two hydroxyl groups attached to non-adjacent carbon atoms. Thus, suitable dihydric alcohols are depicted by the empirical formula

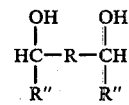

wherein R and R'' are as previously defined. Representative dihydric alcohols which may be used in the process include, 1,3-propanediol; 1,4-butanediol; 2,6-hexandiol; 1,4-heptanediol; 1,4-cyclohexanediol; 2,3-diphenyl-1,4-butanediol; 3-methyl-1,5-pentanediol; diethylene glycol, triethylene glycol, 2-methyl-3-oxahexane diol-1,5 and the like.

It has been found that under the reaction conditions of this process, detailed hereinafter, the hydrogen ions of the hydroxyl groups of the dihydric alcohol are replaced with an alkoxycarboxy group of the formula

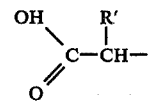

wherein R' is as previously defined. The structure of the alkoxycarboxy group is determined by the choice of saturated aldehyde. For example, by using butyraldehyde as the aldehydric reactant, one can obtain a di(butyloxycarboxy) compound. Similarly, the structure of the hydrocarbylene group will correspond to the structure of the dihydric alcohol. For example, by using 1,4-butanediol as the dihydric alcohol reactant, one can obtain a di(alkoxycarboxy) butylene. Non-adjacent alkanediols are a preferred class of alcohol which are used to obtain di(alkoxycarboxy) alkylenes.

The conditions under which the process of this invention can be carried out are unexpectedly mild. The temperature in the reaction zone may range from about 0° to about 100° C, preferably from about 20° to about 60° C. The carbon monoxide partial pressure may vary from about 10 psia to about 4000 psia, preferably from about 10 psia to about 3000 psia.

The carbon monoxide used in this process can be passed either co-currently or counter-currently to the formaldehyde, and glycol reactants. In a preferred system, a synthesis gas comprising carbon monoxide and hydrogen is passed in cascade fashion past the formaldehyde and glycol reactants and hydrogen fluoride catalyst so that the carbon monoxide is reacted out of the upward flowing stream and a purified gas stream of reduced carbon monoxide content is obtained. The purified hydrogen rich gas can be used in various hydrogenation processes. In addition to hydrogen, the carbon monoxide may be diluted with other inert gases, such as nitrogen or carbon dioxide. In these cases the carbon monoxide partial pressure should exceed 10 psia.

Although the preferred source of carbon monoxide is gaseous carbon monoxide as is obtained in synthesis gas, it is also contemplated that carbon monoxide can be formed in situ by a chemical reaction, e.g., by the decomposition of formic acid into carbon monoxide and water.

In accordance with the practice of this process, the saturated aldehyde, non-adjacent dihydric alcohol, and hydrogen fluoride are fed to the reaction zone at a mol percent of from about 5 to about 35% aldehyde, from about 5 to about 35% alcohol, and from about 50 to about 90% hydrogen fluoride.

The reaction product comprising a di(alkoxycarboxy) hydrocarbylene can be purified using conventional methods.

The following examples illustrate the process of this invention. Those familiar with the art will recognize that various modifications are possible.

EXAMPLES

Example 1 — Preparation of 1,4-Di(methoxy carboxy)-butylene

A 300-ml magnetically stirred stainless-steel autoclave was charged with 0.4 mol of formaldehyde (trioxane), 0.2 mol of 1,4-butanediol and 50 grams of hydrogen fluoride. The autoclave was pressured to 1000 psig with carbon monoxide. The reaction mixture was stirred for 55 minutes during which time the temperature rose from 18° to 29° C. After removal of hydrogen fluoride, the crude product was analyzed and found to comprise:

18% 1,4-di(methoxycarboxy) butylene
54% 4-hydroxybutoxyacetic acid
18% hydroxyacetic acid (glycolic acid)
5% diglycolic acid Example 2 — Preparation of 1,4-Di(methoxy carboxy) butylene The same autoclave used in Example 1 was charged with 0.6 mol of formaldehyde (trioxane), 0.15 mol of 1,4-butanediol and 50 grams of hydrogen fluoride. The autoclave was then pressured to 1000 psig by carbon monoxide. The reaction mixture was stirred for 70 minutes during which time the temperature rose from 23° to 49° C. After removal of the hydrogen fluoride, the crude product was analyzed and found to comprise:

41% 1,4-di(methoxycarboxy)butylene
26% 4-hydroxybutoxyacetic acid
24% glycolic acid
8% diglycolic acid
2% 1,4-butanediol Example 3 — Preparation of 3,6,9-trioxaundecanedioic acid The same reactor used in Example 1 was charged with 0.4 mol of formaldehyde, 0.2 mol of diethylene glycol and 50 grams of hydrogen fluoride. The autoclave was pressured to 1000 psig with carbon monoxide. The reaction mixture was stirred for 55 minutes during which time the maximum temperature reached was 50° C. After removal of the hydrogen fluoride, the product was analyzed and found to comprise:

42% 3,6,9-trioxaundecanedioic acid
29% 8-hydroxy-3,6-dioxaoctanoic acid
29% glycolic acid

What is claimed is:

1. A process for preparing di(alkoxycarboxy) compounds of the formula

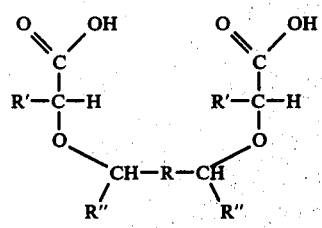

wherein R is straight or branched chain alkylene, oxaalkylene or cycloalkylene; each R' is hydrogen or straight or branched chain alkyl; and each R" is hydrogen, straight or branched alkyl, arylalkyl, haloalkyl or oxaalkyl, which comprises contacting carbon monoxide with a saturated aldehyde and a non-adjacent dihydric alcohol in the presence of a catalytic amount of hydrogen fluoride at a temperature of from about 0° to about 100° C and a carbon monoxide partial pressure of from about 10 psia to about 4000 psia.

2. A process in accordance with claim 1 wherein the temperature is from about 20° to about 60° C.

3. A process in accordance with claim 1 wherein the pressure is from about 10 psia to about 3000 psia.

4. A process in accordance with claim 1 wherein the saturated aldehyde is a $C_1$ to $C_{20}$ aldehyde.

5. A process in accordance with claim 4 wherein the saturated aldehyde is a $C_1$ to $C_{10}$ aldehyde.

6. A process in accordance with claim 1 wherein the non-adjacent dihydric alcohol is a $C_3$ to $C_{20}$ $\alpha,\omega$-alkanediol.

7. A process in accordance with claim 6 wherein the non-adjacent dihydric alcohol is a $C_3$ to $C_{10}$ $\alpha,\omega$-alkanediol.

8. A process in accordance with claim 1 wherein the aldehyde, the alcohol, and hydrogen fluoride are fed to the reaction zone at a mol percent of from about 5 to about 35% aldehyde, from about 5 to about 35% alcohol, and from about 50 to about 90% hydrogen fluoride.

9. A process in accordance with claim 1 wherein the dihydric alcohol is 1,4-butanediol.

10. A process for preparing 1,4-di(alkoxycarboxy) alkylene in accordance with claim 1 which comprises contact carbon monoxide with from about 5 mol % to about 35 mol % of a $C_1$ to $C_{10}$ aldehyde and from about 5 mol % to about 35 mol % of a $C_1$ to $C_{10}$ $\alpha,\omega$-alkanediol in the presence of from about 50 mol % to about 90 mol % of hydrogen fluoride at a temperature of from about 20° to about 60° C and a carbon monoxide partial pressure of from about 10 psia to about 3000 psia.

11. A process in accordance with claim 10 wherein the aldehyde is formaldehyde and the dihydric alcohol is 1,4-butanediol.

* * * * *